United States Patent

Shribbs

[11] Patent Number: 5,741,756
[45] Date of Patent: Apr. 21, 1998

[54] SYNERGISTIC HERBICIDAL COMPOSITION COMPRISING TRIKETONES AND CHLOROACETANILIDES, AND METHOD OF USE THEREOF

[75] Inventor: John Martin Shribbs, Petaluma, Calif.

[73] Assignee: Zeneca Limited, London, England

[21] Appl. No.: 504,267

[22] Filed: Jul. 19, 1995

[51] Int. Cl.$^6$ ............................. A01N 35/06; A01N 37/22
[52] U.S. Cl. ................................................ 504/149
[58] Field of Search ................................... 504/149

[56] References Cited

U.S. PATENT DOCUMENTS

| | | | |
|---|---|---|---|
| 4,146,387 | 3/1979 | Thiele et al. | 504/149 |
| 4,997,473 | 3/1991 | Nguyen | 71/98 |
| 5,006,158 | 4/1991 | Carter et al. | 71/98 |
| 5,089,046 | 2/1992 | Lee et al. | 71/103 |
| 5,407,898 | 4/1995 | Quadranti et al. | 504/149 |
| 5,447,903 | 9/1995 | Ort et al. | 504/138 |
| 5,482,922 | 1/1996 | Suto et al. | 504/149 |
| 5,491,124 | 2/1996 | Quaghebeur | 504/139 |
| 5,506,195 | 4/1996 | Ensminger et al. | 504/350 |
| 5,545,607 | 8/1996 | Quaghebeur et al. | 504/130 |

FOREIGN PATENT DOCUMENTS 42 16 880 11/1993 Germany.

OTHER PUBLICATIONS

Worthing et al., *The Pesticide Manual*, 9th Ed. (1991), pp. 5, 13, 14 and 585.

*Primary Examiner*—S. Mark Clardy
*Attorney, Agent, or Firm*—Marian T. Thomson

[57] ABSTRACT

A synergistic herbicidal composition containing (A) a cyclohexanedione compound of formula (I):

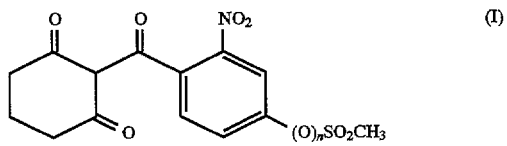

wherein n is 0 or 1; and (B) a chloroacetanilide compound of the formula (II):

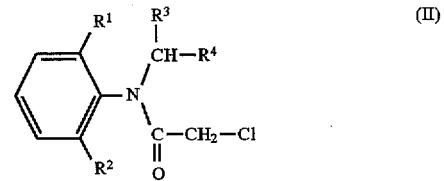

wherein $R^1$ is hydrogen, methyl or ethyl; $R^2$ is hydrogen or ethyl; $R^3$ is hydrogen or methyl; and $R^4$ is methyl, methoxy, methoxymethyl, ethoxy or butoxy. A method of controlling the growth of undesirable vegetation, particularly in crops, using this synergistic composition is also disclosed.

15 Claims, No Drawings

SYNERGISTIC HERBICIDAL COMPOSITION COMPRISING TRIKETONES AND CHLOROACETANILIDES, AND METHOD OF USE THEREOF

FIELD OF THE INVENTION

The present invention relates to a synergistic herbicidal composition containing (A) an herbicidal cyclohexanedione compound and (B) an herbicidal chloroacetanilide compound, together with an agriculturally acceptable carrier therefor. The invention also relates to a method of controlling the growth of undesirable vegetation, particularly in crops, and to the use of this synergistic composition.

BACKGROUND OF THE INVENTION

The protection of crops from weeds and other vegetation which inhibits crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually, and this is referred to as "synergism." As defined in the *Herbicide Handbook* of the Weed Science Society of America, Seventh Edition, 1994, page 318, "'synergism' [is] an interaction of two or more factors such that the effect when combined is greater than the predicted effect based on the response to each factor applied separately." The present invention is based on the discovery that certain cyclohexanediones and certain chloracetanilides, already known individually for their herbicidal efficacy, display a synergistic effect when applied in combination.

The herbicidal compounds forming the synergistic composition of this invention are independently known in the art for their effects on plant growth. The herbicidal cyclohexanedione compound 2-(2'-nitro-4'-methylsulfonylbenzoyl)-1.3-cyclohexanedione ("NMSC") is disclosed in U.S. Pat. No 5,006,158 to Carter et al, and the herbicidal cyclohexanedione compound 2-(2'-nitro-4'-methylsulfonyloxybenzoyl)-1.3-cyclohexanedione ("NMSOC") is disclosed in U.S. Pat. No. 5,089,046 to Lee et al. The chloroacetanilides are a known class of compounds having herbicidal activity. A number of herbicidal chloroacetanilide compounds are described in the *Herbicide Handbook* of the Weed Science Society of America (Seventh Edition, 1994), including 2-chloro-N-(ethoxymethyl)-N-(2-ethyl-6-methylphenyl)acetamide ("acetochlor"),2-chloro-N-(2, 6-diethylphenyl)-N-(methoxymethyl)acetamide ("alachlor"), N-(butoxymethyl)-2-chloro-N-(2,6-diethylphenyl)acetamide ("butachlor"),2-chloro-N-(2-ethyl-6-methylphenyl)-N-(2-methoxy-1-methylethyl)acetamide ("metolachlor") and 2-chloro-N-(1-methylethyl)-N-phenylacetamide ("propachlor"). Many of these chloroacetanilide herbicides are commercially available.

SUMMARY OF THE INVENTION

The present invention relates to a synergistic herbicidal composition containing (A) a cyclohexanedione compound of formula (I):

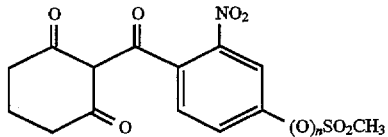

wherein n is 0 or 1: and (B) a chloroacetanilide compound of the formula (II):

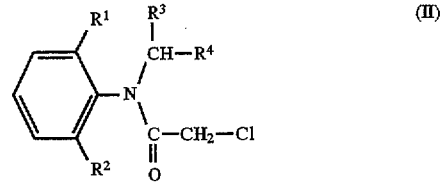

wherein $R^1$ is hydrogen, methyl or ethyl; $R^2$ is hydrogen or ethyl; $R^3$ is hydrogen or methyl; and $R^4$ is methyl, methoxy, methoxymethyl, ethoxy or butoxy. The invention also relates to a method of controlling the growth of undesirable vegetation, particularly in crops, and to the use of this synergistic composition.

The species spectrums of the compounds of formulae (I) and (II), i.e., the weed species which the respective compounds control, are broad and highly complementary. Compounds of formula (I) control most broadleaf weeds and a few grass weeds, and compounds of formula (II) control most grass weeds and a few or some broadleaf weeds. The species spectrum for individual compounds within the scope of each formula varies to some extent. It has been surprisingly found, however, that a combination of a compound of formula (I) and a compound of formula (II) exhibits a synergistic action in the control of common purslane, *Portulaca oleracea* ("POROL"), at rates at which neither a compound of formula (I) nor a compound of formula (II) alone exhibits control of this weed species. POROL is a broadleaf weed, common in the southern United States and pandemic throughout the world, and control of this weed among crops, particularly corn, is highly desirable.

The synergistic composition of the present invention provides a number of advantages over the use of the individual compounds of formulae (I) and (II). First, the rates of application of the individual compounds can be markedly reduced while maintaining a high level of herbicidal efficacy. Second, the synergistic composition has a considerably broader weed spectrum against which it is effective than does either of the compounds alone. Finally, the synergistic composition is capable of controlling weed species at a low application rate at which the individual compounds alone were ineffective.

DETAILED DESCRIPTION OF THE INVENTION

The synergistic herbicidal compositions of this invention contain (A) a compound of formula (I) and (B) a compound of formula (II), wherein formulae (I) and (II) are defined above; and an agriculturally acceptable carrier therefor. Preferably, component (A) is NMSC and component (B) is acetochlor, alachlor or metolachlor, with acetochlor being especially preferred.

The synergistic composition contains an herbicidally effective amount of a combination of component (A) and component (B). The term "herbicide" as used herein denotes a compound which controls or modifies the growth of plants. The term "herbicidally effective amount" indicates the quantity of such a compound or combination of such compounds which is capable of producing a controlling or modifying effect on the growth of plants. Controlling or modifying effects include all deviation from natural development, for example: killing, retardation, leaf burn, albinism, dwarfing and the like. The term "plants" refers to all physical pars of a plant, including seeds, seedlings, saplings, roots, tubers, stems, stalks, foliage, and fruits.

In the compositions of this invention, the weight ratio of component (A) to component (B) at which the herbicidal effect is synergistic lies within the range of between about 32:1 and about 1:20. Preferably, the weight ratio of component (A) to component (B) is between about 8:1 and 1:15, with a weight ratio of between about 4:1 and about 1:10 being especially preferred.

The rate at which the synergistic composition of the invention is applied will depend upon the particular type of weed to be controlled, the degree of control required, and the timing and method of application. In general, the compositions of the invention can be applied at an application rate of between about 0.005 kilograms/hectare (kg/ha) and about 5.0 kg/ha, based on the total amount of active ingredient (component (A)+component (B)) in the composition. An application rate of between about 0.5 kg/ha and 3.0 kg/ha is preferred. In an especially preferred embodiment of this invention, the composition contains components (A) and (B) in relative amounts sufficient to provide an application rate of at least 1.0 kg/ha, of which component (A) provides at least 0.04 kg/ha.

The compositions of this invention are useful as herbicides, demonstrating synergistic activity for the control of undesirable vegetation. The compositions can be formulated in the same manner in which herbicides are generally formulated. The compounds may be applied either separately or combined as part of a two-part herbicidal system.

The object of the formulation is to apply the compositions to the locus where control is desired by a convenient method. The "locus" is intended to include soil, seeds, and seedlings, as well as established vegetation.

The composition employed in the practice of the present invention can be applied in a variety of ways known to those skilled in the art, at various concentrations. The composition is useful in controlling the growth of undesirable vegetation by preemergence or postemergence application to the locus where control is desired. The compositions of the present invention are particularly effective when applied preemergence.

In practice, the composition is applied as a formulation containing the various adjuvants and carriers known to or used in the industry for facilitating dispersion. The choice of formulation and mode of application for any given compound may affect its activity, and selection will be made accordingly. The compositions of the invention may thus be formulated as granules, as wettable powders, as emulsifiable concentrates, as powders or dusts, as flowables, as solutions, as suspensions or emulsions, or as controlled release forms such as microcapsules. These formulations may contain as little as about 0.5% to as much as about 95% or more by weight of active ingredient. The optimum amount for any given compound will depend upon formulation, application equipment, and nature of the plants to be controlled.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, such as xylene, heavy aromatic naphthas, isophorone and other non-volatile organic solvents. In use, these concentrates are dispersed in water or other liquid and normally applied as a spray to the area to be treated. The amount of active ingredient may range from about 0.5% to about 95% of the concentrate.

Granular formulations include both extrudates and relatively coarse particles, and are usually applied without dilution to the area in which suppression of vegetation is desired. Typical carriers for granular formulations include sand, fuller's earth, attapulgite clay, bentonite clays, montmorillonite clay, vermiculite, perlite and other organic or inorganic materials which absorb or which can be coated with the active compound. Granular formulations normally contain about 5% to about 25% active ingredients which may include surface-active agents such as heavy aromatic naphthas, kerosene and other petroleum fractions, or vegetable oils; and/or stickers such as dextrins, glue or synthetic resins.

Dusts are flee-flowing admixtures of the active ingredient with finely divided solids such as talc, clays, flours and other organic and inorganic solids which act as dispersants and carriers.

Microcapsules are typically droplets or granules of the active material enclosed in an inert porous shell which allows escape of the enclosed material to the surroundings at controlled rates. Encapsulated droplets are typically about 1 to 50 microns in diameter. The enclosed liquid typically constitutes about 50 to 95% of the weight of the capsule, and may include solvent in addition to the active compound. Encapsulated granules are generally porous granules with porous membranes sealing the granule pore openings, retaining the active species in liquid form inside the granule pores. Granules typically range from 1 millimeter to 1 centimeter, preferably 1 to 2 millimeters in diameter. Granules are formed by extrusion, agglomeration or prilling, or are naturally occurring. Examples of such materials are vermiculite, sintered clay, kaolin, attapulgite clay, sawdust and granular carbon. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as acetone, alkylated naphthalenes, xylene and other organic solvents. Pressurized sprayers, wherein the active ingredient is dispersed in finely-divided form as a result of vaporization of a low boiling dispersant solvent carrier, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents, when used, normally comprise from 0.1% to 15% by weight of the formulation.

Each of the above formulations can be prepared as a package containing the herbicide together with other ingredients of the formulation (diluents, emulsifiers, surfactants, etc.). The formulations can also be prepared by a tank mix method, in which the ingredients are obtained separately and combined at the grower site.

These formulations can be applied to the areas where control is desired by conventional methods. Dust and liquid compositions, for example, can be applied by the use of power-dusters, broom and hand sprayers and spray dusters. The formulations can also be applied from airplanes as a dust or a spray or by rope wick applications. To modify or control growth of germinating seeds or emerging seedlings, dust and liquid formulations can be distributed in the soil to a depth of at least one-half inch below the soil surface or applied to the soil surface only, by spraying or sprinkling. The formulations can also be applied by addition to irrigation water. This permits penetration of the formulations into the soil together with the irrigation water. Dust compositions, granular compositions or liquid formulations applied to the surface of the soil can be distributed below the surface of the soil by conventional means such as discing, dragging or mixing operations.

An important factor influencing the usefulness of a given herbicide is its selectivity towards crops. In some cases, a beneficial crop is susceptible to the effects of the herbicide. To be effective, an herbicide must cause minimal damage (preferably no damage) to the beneficial crop while maximizing damage to weed species which infest the locus of the crop. It is known that chloroacetanilide compounds of formula (II) may cause undesirable damage to certain crop species, particularly corn, at relatively high application rates. To preserve the beneficial aspects of herbicide use and to minimize crop damage, it is known to apply chloroacetanilide herbicides in combination with an antidote. As used herein, "antidote" describes a compound which has the effect of establishing herbicide, selectivity, i.e., continued herbicidal phytotoxicity to weed species by the herbicide, and reduced or non-phytotoxicity to the cultivated crop species. The term "antidotally effective amount" describes an amount of an antidote compound which counteracts to some degree a phytotoxic response of a beneficial crop to an herbicide. If necessary or desired for a particular application or crop, the composition of the present invention may contain an antidotally effective amount of an antidote for component (B). Those skilled in the art will be familiar with antidotes which are suitable for use with chloroacetanilide compounds of formula (II) and can readily determine an antidotally effective amount for a particular compound and application.

Further, other biocidally active ingredients or compositions may be combined with the synergistic herbicidal composition of this invention. For example, the compositions may contain, in addition to components (A) and (B), insecticides, fungicides, bactericides, acaracides or nematicides, in order to broaden the spectrum of activity.

The following example is for illustrative purposes only. This example is not intended as necessarily representative of the overall testing performed and is not intended to limit the invention in any way. As one skilled in the art is aware, in herbicidal testing, a significant number of factors that are not readily controllable can affect the results of individual tests and render them non-reproducible. For example, the results may vary depending on environmental factors, such as amount of sunlight and water, soil type, pH of the soil, temperature, and humidity, among other factors. Also, the depth of planting, the application rate of individual and combined herbicides, the application rate of any antidote, and the ratio of the individual herbicides to one another and/or to an antidote, as well as the nature of crops or weeds being tested, can affect the results of the test. Results may vary from crop to crop within the crop varieties.

EXAMPLE

Seeds of the following six different weed species were sown into 1 liter aluminum flats containing sandy loam soil: barnyardgrass (*Echinochloa crusgalli*) ("ECHCG"), goosegrass (*Eleusine indica*) ("ELEIN"), wild-proso millet (*Panicum miliaceum*) ("PANMI"), large crabgrass (*Digitaria sanguinalis*) ("DIGSA"), broadleaf signalgrass (*Brachiaria platphylla*) ("BRAPP"), and POROL. Seeding depths ranged from 0.5 to 1.5 cm and plant densities ranged from 3 to 25 plants per row depending on individual plant species. Seeds of ivyleaf morningglory (*Ipomoea hederacea*) ("IPOHE") were sown into 400 ml plastic cups containing sandy loam soil.

Water dispersible formulations of NMSC and acetochlor were applied to the soil surface in a complete factorial treatment design with seven (7) levels of each. NMSC was applied at 0, 5, 10, 20, 40, 80 and 160 grams per hectare (g/ha) to the flats and to the cups. Acetochlor was applied at 0, 5, 10, 20, 40, 80 and 160 g/ha to the flats and at 0, 50, 100, 200, 400, 800 and 1600 g/ha to the cups. After application, the flats and cups were placed in a glasshouse and maintained under good growing conditions.

The degree of weed control was visually evaluated and recorded 25 days after treatment as a percentage of weed control. Percent control is the total injury to the plants due to all factors including: inhibited emergence, stunting, malformation, chlorosis and other types of plant injury. The control ratings range from 0 to 100 percent, where 0 represents no injury and 100 represents complete kill.

The combination of NMSC and acetochlor was effective against the tested weed species at varying rates of application. The combinations of NMSC and acetochlor gave various results against PANMI, ECHCG, DIGSA, ELEIN, BRAPP and IPOHE, showing antagonism, additivity and synergy or an indication of potential synergy at different levels of application. However, it was found that combinations of NMSC and acetochlor exhibited unexpected and surprising synergistic action in the control of POROL, at rates at which neither compound alone exhibits control of this weed species.

Table I below shows the actual results of the above described preemergence testing of combinations of NMSC and acetochlor on POROL. Table I also shows the expected weed control for the tested combinations of NMSC and acetochlor against POROL, calculated according to the Colby method (S. R. Colby. "Calculating Synergistic and Antagonistic Response of Herbicide Combinations." WEEDS 15(I):20–23, 1967). The Colby method represents a direct approach to measuring the synergistic activity of two herbicides. According to the Colby method:

$$E = X + Y - (XY/100),$$

wherein E is the expected percent weed control for a combination of a first herbicide H1 and a second herbicide H2 at an application rate of p+q g/ha; X is the percent weed control observed for H1 at application rate p g/ha; and Y is the percent weed control observed for H2 at application rate q g/ha.

TABLE I

Weed Control of POROL by Combinations of NMSC and Acetochlor

| NMSC (g/ha) | Acetochlor (g/ha) | | | | | | | | | | | | |
|---|---|---|---|---|---|---|---|---|---|---|---|---|---|
| | 0 | | 5 | | 10 | | 20 | | 40 | | 80 | | 160 | |
| | A[1] | E[2] | A | E | A | E | A | E | A | E | A | E | A | E |
| 0 | 0 | 0 | 0 | 0 | 0 | 0 | 0 | 0 | 0 | 0 | 12 | 12 | 45 | 45 |
| 5 | 0 | 0 | 0 | 0 | 0 | 0 | 0 | 0 | 0 | 0 | 17 | 12 | 45 | 45 |
| 10 | 0 | 0 | 0 | 0 | 0 | 0 | 0 | 0 | 0 | 0 | 17 | 12 | 70 | 45 |
| 20 | 0 | 0 | 0 | 0 | 0 | 0 | 0 | 0 | 0 | 0 | 22 | 12 | 33 | 45 |
| 40 | 0 | 0 | 0 | 0 | 0 | 0 | 0 | 0 | 5 | 0 | 77 | 12 | 88 | 45 |
| 80 | 5 | 5 | 0 | 5 | 83 | 5 | 60 | 5 | 77 | 5 | 100 | 16 | 100 | 48 |
| 160 | 5 | 5 | 55 | 5 | 47 | 5 | 62 | 5 | 72 | 5 | 100 | 16 | 100 | 48 |

[1] Actual percent weed control
[2] Expected percent weed control

The results shown in Table I demonstrate the synergistic herbicidal efficacy achieved by compositions of this invention.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. An herbicidal composition comprising an herbicidally effective amount of a mixture of:

(A) a cyclohexanedione compound of formula (I):

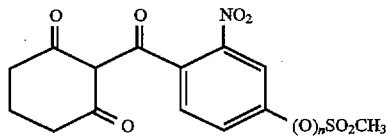

wherein n is 0 or 1; and (B) a chloroacetanilide compound selected from the group consisting of acetochlor, alachlor and metolachlor.

2. An herbicidal composition according to claim 1, wherein component (A) is 2-(2'-nitro-4'-methylsulfonylbenzoyl)-1,3-cyclohexanedione.

3. An herbicidal composition according to claim 1, wherein component (B) is acetochlor.

4. An herbicidal composition according to claim 1, wherein the weight ratio of component (A) to component (B) is between about 32:1 and about 1:20.

5. An herbicidal composition according to claim 4, wherein the weight ratio of component (A) to component (B) is between about 8:1 and 1:15.

6. An herbicidal composition according to claim 4, wherein the weight ratio of component (A) to component (B) is between about 4:1 and about 1:10.

7. A method for controlling undesirable vegetation, comprising applying to the locus of such vegetation an herbicidally effective amount of a composition comprising (A) a cyclohexanedione compound of formula (I):

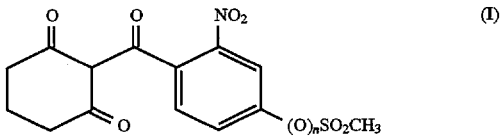

wherein n is 0 or 1; and (B) a chloroacetanilide compound selected from the group consisting of acetochlor, alachlor and metolachlor.

8. A method according to claim 7, wherein component (A) of said composition is 2-(2'-nitro-4'-methylsulfonylbenzoyl)-1,3-cyclohexanedione.

9. A method according to claim 7, wherein component (B) is acetochlor.

10. A method according to claim 7, wherein the weight ratio of component (A) to component (B) in said composition is between about 32:1 and about 1:20.

11. A method according to claim 10, wherein the weight ratio of component (A) to component (B) is between about 8:1 and 1:15.

12. A method to claim 10, wherein the weight ratio of component (A) to component (B) is between about 4:1 and about 1:10.

13. A method according to claim 7, wherein the combined amount of components (A) and (B) applied to the locus of the undesirable vegetation is between about 0.005 kg/ha and about 5.0 kg/ha.

14. A method according to claim 13, wherein the combined amount of components (A) and (B) applied to the locus of the undesirable vegetation is between about 0.5 kg/ha and 3.0 kg/ha.

15. A method according to claim 7, wherein the combined amount of components (A) and (B) applied to the locus of the undesirable vegetation is at least 1.0 kg/ha, and wherein at least 0.04 kg/ha of component (A) is applied to the locus of the undesirable vegetation.

* * * * *